US008236243B2

(12) United States Patent
Palena et al.

(10) Patent No.: US 8,236,243 B2
(45) Date of Patent: Aug. 7, 2012

(54) NANO-GETTER DEVICE

(75) Inventors: Patricia D. Palena, Plainsboro, NJ (US); Richard R. Barto, Jr., Avondale, PA (US); Tammie L. Borders, Justin, TX (US); Jeffrey A. Stuart, Columbia, CT (US)

(73) Assignee: Lockheed Martin Corporation, Bethesda, MD (US)

( * ) Notice: Subject to any disclaimer, the term of this patent is extended or adjusted under 35 U.S.C. 154(b) by 758 days.

(21) Appl. No.: 12/348,128

(22) Filed: Jan. 2, 2009

(65) Prior Publication Data

US 2009/0220382 A1   Sep. 3, 2009

Related U.S. Application Data

(60) Provisional application No. 61/018,774, filed on Jan. 3, 2008.

(51) Int. Cl.
  *G01N 27/00* (2006.01)
  *A61B 5/145* (2006.01)
(52) U.S. Cl. .................... 422/82.01; 600/309
(58) Field of Classification Search ............. 422/82.01
  See application file for complete search history.

(56) References Cited

U.S. PATENT DOCUMENTS

| | | | |
|---|---|---|---|
| 5,418,136 A | 5/1995 | Miller | |
| 5,866,430 A * | 2/1999 | Grow | 506/6 |
| 6,617,040 B2 * | 9/2003 | Houser et al. | 428/447 |
| 7,045,367 B2 | 5/2006 | Kaganove et al. | |
| 2003/0109056 A1 | 6/2003 | Vossmeyer et al. | |
| 2003/0135971 A1 | 7/2003 | Liberman et al. | |
| 2005/0089890 A1 | 4/2005 | Cubicciotti | |
| 2006/0054506 A1 | 3/2006 | Natan et al. | |
| 2006/0191320 A1 | 8/2006 | Pinnaduwage et al. | |
| 2007/0212746 A1 | 9/2007 | Bauer | |
| 2008/0114077 A1 | 5/2008 | Yin et al. | |

FOREIGN PATENT DOCUMENTS

WO   2006102484   9/2006

OTHER PUBLICATIONS

J.A. Ludwig and J. N. Weinstein, "Biomarkers in cancer staging, prognosis and treatment selection", Nat. Rev. Cancer, 5(11), 2005, pp. 845-856.
R.J. Buckanovich et al., "Tumor vascular proteins as biomarkers in ovarian cancer", J. Clin. Oncology, 25(7), 2007, pp. 852-861.
M. Mallardo et al., "Non-protein coding RBA biomarkers and differential expression in cancers; a review", J. Exp. & Clin. Cancer Res., 27(19), 2008, doi:10.1186/1756-9966-27-19.
A. Priebe and R. J. Buckanovich (Priebe et al), "Ovariantumor vasculature as a source of biomarkers for diagnosis and therapy", Expert Rev. Obstet. Gynecol., 3(1), 2008, pp. 65-72.
Z.Zhang et al., "Three biomarkers identified from serum proteomic analysis for the detection of early stage ovarian cancer", Cancer Res., 64(16) pp. 5882-5890.
Urs. Utzinger et al, "Near-Infrared Raman Spectroscopy for In Vivo Detection of Cervical Precancers", Applied Spectroscopy v. 55, No. 8, 2001, pp. 955-959.
The A to Z of Nanotechnology, "Dendrimers: Definition, Dendrimers in Medicine, Other Industry Applications and Examples of Products", ETC Group report entitled 'Nanotech's "Second Nature" Patents: Implications for the Global South', Apr./May 2005.
Dr. Jose Feneque, "Brief Introduction to the Veterinary Applications of Nanotechnology", Nanotechnology Now, Dec. 2003.
ANS Dendrimer Review: Construction, "The Construction of Dendrimers", www.ninger.com/dendimer/two.htm.
The National Dendrimer & Nanotechnology Center, "What are Dendrimers", www.dendrimercenter.org/dendrimers.html.
Li et al., Electrochemical Impedance Detection of DNA Hybridization Based on Dendrimer Modified Electrode, Biosensors and Bioelectronics 22 (2007) pp. 1716-1722.
European Search Report for counterpart European Application No. 09700124.2, mailed Aug. 19, 2011, 7 pgs.

* cited by examiner

*Primary Examiner* — Randy Boyer
(74) *Attorney, Agent, or Firm* — Clise, Billion & Cyr, P.A.; Richard E. Billion

(57) ABSTRACT

A nano-structured device for detecting biological analytes, chemical, analytes, cancer and other physiological conditions, includes a carrier substrate, a transducer film disposed over a surface of the carrier substrate, and a dendrimer structure tethered to the transducer film. The transducer film generates a first signal in response to a mechanical stress applied thereto. The first signal indicates the detection of the biological analyte, chemical analyte, cancer or other physiological condition. The dendrimer structure includes a plurality of receptors for binding the biological analyte, the chemical analyte, or one or more biomarkers indicative of cancer or other physiological conditions to the dendrimer structure. The dendrimer structure applies the mechanical stress to the transducer film, which is proportional to the strain induced into the dendrimer by the biological analyte, the chemical analyte, or one or more biomarkers indicative of cancer or other physiological condition binding to the receptors, the mechanical stress causing the transducer film to generate the first signal indicating the detection of the biological analyte, the chemical analyte, or one or more biomarkers indicative of cancer or other physiological condition.

26 Claims, 3 Drawing Sheets

NANO-GETTER DEVICE

RELATED APPLICATIONS

The application claims the benefit of U.S. Provisional Application No. 61/018,774, filed Jan. 3, 2008, the entire disclosure of which is incorporated herein by reference.

FIELD OF THE INVENTION

This invention relates to nano-structured devices. More particularly, this invention relates to nanostructured devices for detecting biological and chemical substances.

BACKGROUND OF THE INVENTION

Early detection of ovarian cancer is very difficult because symptoms do not usually become evident until the disease is in the later stages of development. The radiological scanners used to detect tumors are limited to cm resolution, which is poor at best when cancer cells are on the order of 10 s-100 s of microns in size. Early detection of ovarian and other cancers typically extends the life expectancy significantly compared to later stage diagnosis.

Accordingly, a device is needed which can detect cancer in its early stages.

SUMMARY

Disclosed herein is a nano-structured device for detecting a chemical or biological analyte, comprising a carrier substrate, a transducer film disposed over a surface of the carrier substrate, and a dendrimer structure tethered to the transducer film. The transducer film generates a first signal in response to a mechanical stress applied thereto. The first signal indicates the detection of the chemical or biological analyte. The dendrimer structure includes a plurality of receptors for binding molecules of the chemical or biological analyte to the dendrimer structure. The dendrimer structure applies the mechanical stress to the transducer film, which is proportional to the strain induced into the dendrimer by the molecules of the chemical or biological analyte binding to the receptors, the mechanical stress causing the transducer film to generate the first signal indicating the detection of the chemical or biological analyte.

Also disclosed herein is a nanostructured device for detecting a chemical or biological analyte, comprising a carrier substrate for generating a signal which changes in proportion to a mass increase of the nano-structured device, a transducer film disposed over a surface of the carrier substrate, and a dendrimer structure tethered to the transducer film. The signal generated by the carrier substrate indicates the detection of the chemical or biological analyte. The dendrimer structure includes a plurality of receptors for binding molecules of the chemical or biological analyte to the dendrimer structure, wherein the mass increase is proportional to the quantity of molecules binding to the dendrimer structure via the receptors, the mass increase causing the carrier substrate to generate the signal indicating the detection of the chemical or biological analyte.

Further disclosed herein is a nano-structured device for detecting cancer or other physiological conditions, comprising a carrier substrate, a transducer film disposed over a surface of the carrier substrate, and a dendrimer structure tethered to the transducer film. The transducer film generates a first signal in response to a mechanical stress applied thereto, the first signal indicating the detection of the cancer or other physiological condition. The dendrimer structure includes a plurality of receptors for binding biomarkers specific to the presence of cancerous cells or other physiological conditions. Upon interaction of the biomarker with the receptors of the dendrimer structure (functionalized dendrimer structure), a mechanical stress is applied to the transducer film, which is proportional to the strain induced into the dendrimer by the biomarkers binding to the receptors, the mechanical stress causing the transducer film to generate the first signal indicating the detection of the cancer or other physiological condition.

Still further disclosed herein is a nano-structured device for detecting cancer or other physiological conditions, comprising a carrier substrate for generating a signal which changes in proportion to a mass increase of the nano-structured device, a transducer film disposed over a surface of the carrier substrate, and a dendrimer structure tethered to the transducer film. The signal generated by the carrier substrate indicates the detection of the cancer or other physiological condition. The dendrimer structure includes a plurality of receptors for binding biomarkers specific to the cancer or other physiological condition to the dendrimer structure, wherein the mass increase proportional to the quantity of the biomarkers binding to the dendrimer structure via the receptors, the mass increase causing the carrier substrate to generate the signal indicating the detection of the cancer or other physiological condition.

Also disclosed is an in vivo method for detecting cancer or other physiological conditions. The method comprises providing at least one nano-structured device in a patient's abdominal cavity, the at least one nano-structured device comprising a carrier substrate, a transducer film disposed over a surface of the carrier substrate, at least one of the transducer film and the carrier substrate for generating a signal indicating the detection of the cancer or other physiological condition, and a dendrimer structure tethered to the transducer film, the dendrimer structure including a plurality of receptors for binding biomarkers specific to the cancer or other physiological condition to the dendrimer structure, the dendrimer structure causing the at least one of the transducer film and carrier to generate the signal if the biomarkers for the cancer or other physiological condition are binding to the receptors. Once the at least one nano-structured device has been provided in the patient's abdominal cavity, the at least one device is interrogated and the earlier mentioned signal is obtained if the biomarkers for the cancer or other physiological condition are binding to the receptors of the at least one nano-structured device.

Additionally disclosed is an ex vivo method for detecting cancer or other physiological conditions. The method comprises providing at least one nano-structured device comprising a carrier substrate, a transducer film disposed over a surface of the carrier substrate, at least one of the transducer film and the carrier substrate for generating a signal indicating the detection of the cancer or other physiological condition, and a dendrimer structure tethered to the transducer film, the dendrimer structure including a plurality of receptors for binding biomarkers specific to the cancer or other physiological condition to the dendrimer structure, the dendrimer structure causing the at least one of the transducer film and carrier to generate the signal if the biomarkers for the cancer or other physiological condition are binding to the receptors. Further, the at least one nano-structured device is exposed to a bodily fluid, which may contain the biomarkers for the cancer or other physiological condition, and then interrogated. The earlier mentioned signal is obtained, if the biomarkers for the cancer or other physiological condition are binding to the receptors of the at least one nano-structured device.

Further disclosed is a method for detecting chemical or biological analytes. The method comprises providing at least one nano-structured device comprising a carrier substrate, a transducer film disposed over a surface of the carrier substrate, at least one of the transducer film and the carrier substrate for generating a signal indicating the detection of the chemical or biological analyte, and a dendrimer structure tethered to the transducer film, the dendrimer structure including a plurality of receptors for binding molecules of the chemical or biological analyte to the dendrimer structure, the dendrimer structure causing the at least one of the transducer film and carrier to generate the signal if the molecules are binding to the receptors. Next, the at least one nano-structured device is exposed to an environment, which may contain the molecules of the chemical or biological analyte, and then interrogated. The earlier mentioned signal is obtained if the molecules of the chemical or biological analytes are binding to the receptors of the at least one nano-structured device.

Still further, a device is disclosed which comprises a plurality of differently functionalized nano-structured devices. Each of the nano-structured devices comprises a carrier substrate, a transducer film disposed over a surface of the carrier substrate, at least one of the transducer film and the carrier substrate for generating a signal indicating the detection of chemical analytes, biological analytes, cancer or other physiological conditions, and a dendrimer structure tethered to the transducer film, the dendrimer structure including a plurality of receptors for binding molecules of the chemical or biological analytes or for binding biomarkers specific to the cancer or other physiological condition, to the dendrimer structure, thereby causing the at least one of the transducer film and carrier to generate the signal if the molecules or biomarkers are binding to the receptors. The nano-structured devices of the device are capable of being individually interrogated.

DETAILED DESCRIPTION OF THE INVENTION

Figure 1:
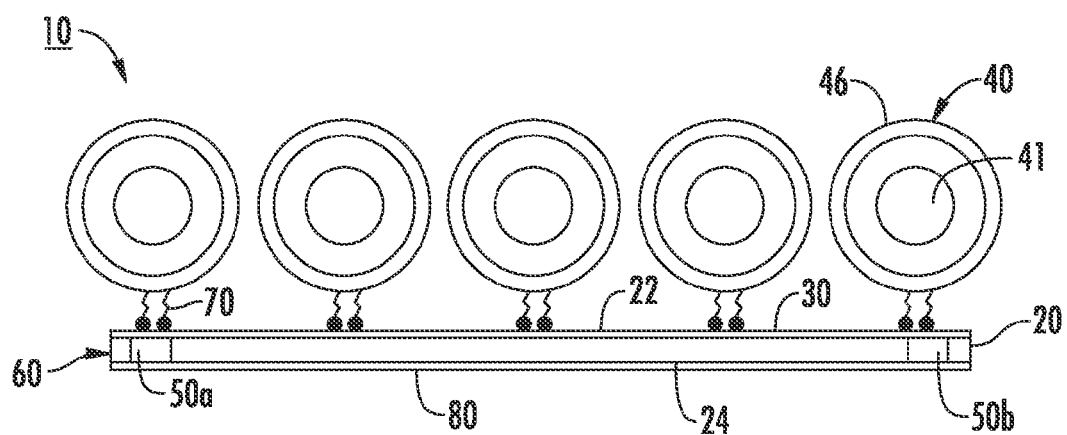
FIG. 1 is an elevational view of an exemplary embodiment of a nano-structured device for in-vivo detection of cancer or other physiological conditions (nano-getter device).

FIG. 1 illustrates an exemplary embodiment of a nano-structured device for detection of cancer or other physiological conditions (nano-getter device), denoted by reference character 10. As shown therein, the nano-getter device 10 comprises a carrier substrate 20, a thin, strain-transducer film 30 disposed on a first surface 22 of the carrier substrate 20, a hydrophobic and inert layer 80 disposed on a second surface of the carrier substrate 20, and one or more ligand-functionalized dendrimers 40 tethered to the thin, strain-transducer film 30. Each dendrimer 40 has one or more binding receptors (ligands) 46 which are capable of gathering biomarkers specific to the cancer or other physiological condition to be detected. In this context, the term biomarker denotes the presence of any protein or other biological molecule that specifically relates to an existing physiological condition within a tissue or environment of interest (e.g., cancer, chemical contaminant, biotoxin, etc.). The nano-getter device 10 is intended for use in in vivo and ex vivo diagnostic methods. An in vivo diagnostic method, in one non-limiting exemplary embodiment, comprises the nano-getter device 10 residing in the abdominal cavity of a patient and screening for the presence of condition-specific (e.g., cancer) biomarkers. An ex vivo diagnostic method, in one non-limiting exemplary embodiment, comprises using an appropriately functionalized nano-getter for external diagnostics, as part of routine blood and/or urine analysis. The nano-getter device 10 is capable of providing two different types of signals indicating a binding event, which greatly reduces the likelihood of false positives, providing greater confidence in the detection method.

The nano-getter device 10 facilitates the in vivo diagnostic methods and applications disclosed herein (e.g., detection of ovarian cancer) because it is very small and innocuous, so that one or more nano-getter devices 10 may be injected as a dialysate suspension into the patient's abdominal cavity, disperse into the peritoneum cavity, and reside for subsequent interrogation by external sensing probes, including but not limited to microwave, ultrasonic, and/or Raman spectroscopy. Typically, ten to several hundred nano-getter devices 10 may be injected as the dialysate suspension into the patient's abdominal cavity for dispersion into the peritoneum cavity. The nano-getter devices 10 may then be ejected from the peritoneal region through a peritoneal dialysate flush.

Ex vivo diagnostic methods and applications include routine medical screenings for a variety of conditions, including, but not limited to, ovarian and prostate cancers. Such applications are facilitated by the availability of the appropriate biomarkers for each condition. In one exemplary non-limiting embodiment, one or more nano-getter based devices may be embedded on a platform suitable for external diagnosis and used to screen blood, urine, or other bodily fluids for a variety of conditions.

The dimensions of the nano-getter device 10 are typically about 0.5 mm or less per side. It should be understood, however, that other embodiments of the nano-getter device 10 may have dimensions which are somewhat greater than 0.5 mm per side.

The carrier substrate 20 is made of a material that is capable of generating a first detection signature modality or signal that changes in proportion with the mass of the nano-getter device. In one embodiment, the carrier substrate 20 comprises a stress-compensated cut (SC-cut), alpha-quartz crystal microbalance (QCM) substrate with first and second integrated/passivated RF dipole electrodes 50a and 50b disposed on an edge of the substrate 20. The carrier substrate 20 typically has a length of about 0.3 mm to about 0.5 mm, a width of about 0.3 mm to about 0.5 mm, and a thickness of about 10 µm, although other carrier substrate sizes may be used. The QCM carrier substrate 20 and the first and second electrodes 50a and 50b form an RF QCM oscillator 60 which generates a resonant harmonic frequency that changes in proportion with the mass of the nano-getter device 10, when the QCM oscillator 60 is excited by an external microwave pulse. In alternate embodiments, other means may be used for externally exciting the QCM oscillator 60, such as RF waveforms in the VHF to UHF range.

The thin, strain-transducer film 30 is made of a material that is capable of generating a second detection signature modality or signal in response an applied mechanical stress. In one exemplary embodiment, the thin, strain-transducer film 30 comprises a Raman-active film. The Raman-active film 30, in one embodiment, is a nanocomposite comprising a polymer film doped with Raman-active, single-wall carbon nanotubes (SWNT). The polymer film may comprise a commercially available thermoplastic approved for medical implant use, such as polyethylene and poly-ether-ether-ketone (PEEK). In one embodiment, the SWNTs may comprise between about 0.1 and about 2.0 weight percent of the polymer film.

The dendrimers 40 may be disposed in a one, two, or three dimensional array, or as a continuous tethered layer of a given average surface areal density. In one embodiment, the dendrimers are disposed in a one or two dimensional array that forms a self-assembled molecular monolayer film.

Figure 2:
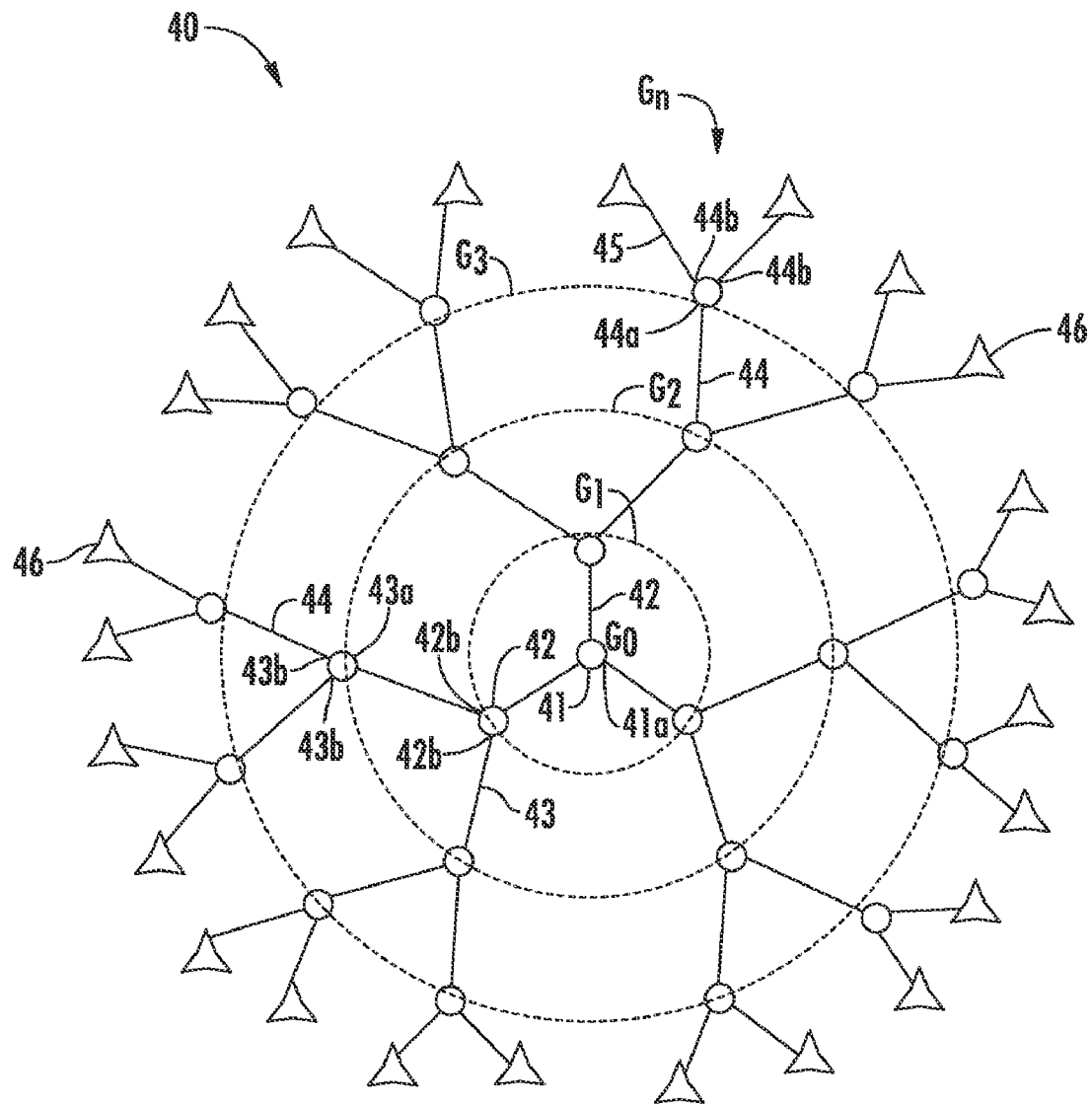
FIG. 2 is a schematic view which shows an exemplary embodiment of a dendrimer.

Each dendrimer 40 is a nanostructure comprising a large molecule formed by branching monomers that define a substantially monodisperse (low polydispersity), generational structure. Each dendrimer 40 typically has but is not limited to a generally spheroid shape. The dendrimers 40 may be synthesized using well-known divergent or convergent stepwise methods. In such methods, the dendrimers 40 are constructed one monomer layer, or "generation," at a time. FIG. 2 shows an exemplary embodiment of one of the dendrimers 40. As can be seen, the dendrimer 40 comprises a core molecule 41, which is referred to as generation $G_0$. The core molecule 41 operates as a branch point and includes a plurality of functional sites 41a. A first plurality of branch monomer units 42 are attached to the functional sites 41a of the core molecule 41, such that each functional site 41a attaches at least one of the plurality of branch monomer units 42. The first plurality of branch monomer units 42 form a first monomer layer or generation $G_1$. If no other monomer layers are synthesized, the dendrimer is referred to as a generation $G_1$ dendrimer and the first monomer layer forms the (outer) surface of the dendrimer. If other monomer layers are synthesized, each successive monomer layer forms a next generation. The dendrimer 40 further includes second, third, and fourth monomer layers $G_2$, $G_3$, and $G_4$, respectively. The second monolayer $G_2$ is formed by a second plurality of branch monomer units 43, each of which is attached to a functional site 42b on a corresponding branch point 42a defined by the first plurality of branch monomer units 42 of generation $G_1$. The third monomer layer $G_3$ is formed by a third plurality of branch monomer units 44, each of which is attached to a functional site 43b on a corresponding branch point 43a defined by the second plurality of branch monomer units 43 of generation $G_2$. The fourth or final monomer layer $G_n$, where n is the number of monomer layers added to the dendrimer 40, is formed by a fourth plurality of branch monomer units 45, each of which is attached to a functional site 44b on a corresponding branch point 44a defined by the third plurality of branch monomer units 44 of generation $G_3$. Each branch monomer unit 45 of the monomer layer $G_n$ includes a ligand functionalized terminus 46.

In other embodiments, the dendrimers 40 used in the nano-getter device 10 may comprise any suitable number of monomer layers or generations. Typical embodiments of the nano-getter device 10 may use generation $G_2$ to generation $G_5$ dendrimers 40. In one exemplary embodiment, the dendrimers 40 may have a polydispersity of less than 1.2. In other embodiments, the dendrimers 40 may have a polydispersity of some other value. As stated earlier, the dendrimers disclosed herein may be synthesized using well known divergent and convergent processes. The divergent method generally comprises synthesizing the core first and then synthesizing each successive monolayer or generation. The convergent method generally comprises synthesizing the final generation or outer monolayer first, synthesizing any intermediate monolayers or generations next, and then finishing with the synthesis of the core.

The ligand-functionalized termini 46 that form the binding receptors in the outer monolayer $G_n$ of each dendrimer 40, may be formed by substituting amine groups with acetamide, carboxylic acid, or any other suitable acid ester end-capping moiety. Each ligand-functionalized terminus 46 is selected to attract and bind a biomarker (typically a protein) specific to the cancer or other physiological condition to be detected, to its corresponding dendrimer 40. Thus, as the nano-getter device 10 is exposed to its target biomarkers or other analyte, either through ex vivo diagnostics or as it travels through the body of the patient and encounters the cancer or other physiological condition to be detected, the biomarker(s) specific to the cancer or other physiological condition are attracted to the receptors 46 in the outer monolayer $G_n$ or surface of each dendrimer 40 and become attach or bound thereto.

Biomarkers specific to a variety of cancers and other physiological conditions have been and continue to be identified in the literature. Typically these take the form of small proteins and peptides, but RNA-and DNA-based markers are also known—many biomarkers are released into a variety of body fluids, including (among others) blood serum, urine, sputum, and nipple aspirates. In the present disclosure, biomarkers will bind to specific receptors attached to dendrimers 40. A non-limiting example of a receptor may be an antibody (monoclonal or polyclonal) that selectively binds a specific biomarker (referred to as the antigen to that antibody). One commonly recognized example is PSA, or prostate-specific antigen. A number of recent advances have identified numerous biomarkers for ovarian cancer, especially with the discovery that ovarian tumor vasculature is a particularly valuable source of specific markers. The emerging fields of bioinformatics (proteomics, transcriptomics, etc.) are providing a wealth of potential biomarkers. The functionalization of the terminus 46 of the dendrimers 40 may be selected to attract and bind these biomarkers to enable the nano-getter device 10 to detect various types of cancers and other physiological conditions. Patterns of gene expression and regulation of different markers (as evidenced through proteomics and transcriptomics), i.e., how the concentrations of specific markers change with respect to one another, may be attracted by suitably adapted nano-getter devices of the present disclosure. Most of the newly identified biomarkers, however, remain to be fully characterized; the presence of markers is indicated through gene expression (transcriptomics) or proteomics, but specific properties have not yet been determined. However, progress is being made toward this end. See, for example, J. A. Ludwig and J. N. Weinstein (Ludwig et al.), *Biomarkers in cancer staging, prognosis and treatment selection*, Nat. Rev. Cancer, 5(11), 2005, pp. 845-856; R. J. Buckanovich et al., *Tumor vascular proteins as biomarkers in ovarian cancer*, J. Clin. Oncology, 25(7), 2007, pp. 852-861; M. Mallardo et al., *Non-protein coding RNA biomarkers and differential expression in cancers: a review*, J. Exp. & Clin. Cancer Res., 27(19), 2008, doi: 10.1186/1756-9966-27-19; and A. Priebe and R. J. Buckanovich (Priebe et al.), *Ovarian tumor vasculature as a source of biomarkers for diagnosis and therapy*, Expert Rev. Obstet. Gynecol., 3(1), 2008, pp. 65-72. The disclosures of Ludwig et alt, Buckanovich et al., Mallardo et al., and Priebe et al. are incorporated herein by reference.

Figure 3:
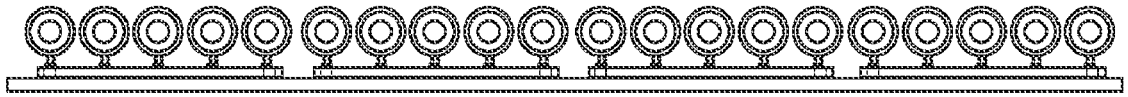
FIG. 3 is an elevational view of an exemplary embodiment of a device including a plurality of nano-structured devices.

Once individual biomarkers have been identified and characterized, the generally-accepted approach is to generate antibodies that will bind specifically to each biomarker. The same antibodies can be used to functionalize the nano-getter dendrimers 40 at termini 46. For the specific case of prostate-specific antigen, antibodies are commercially available. Several biomarkers (or antigens) have been identified for ovarian cancer, including CA125, apolipoprotein A1, a truncated form of transthyretin, and a fragment of inter-a-trypsin inhibitor heavy chain H4, although the pattern with which these (and others) are expressed is important (see reference below). By the appropriate functionalization of multiple dendrimers 40 with antigen specific antibodies, the nano-getter can be adapted to detect patterns associated with the onset of ovarian and other cancers. In one non-limiting exemplary embodiment, as shown in FIG. 3, a device containing a plurality of individually-interrogated, uniquely functionalized nano-getter devices (i.e., the dendrimers 40 of each individual device functionalized for a specific, unique biomarker) organized, for example, in a tethered array or a tethered continuous layer. Such a device may be used to detect cancers or other physiological conditions based on the pattern of biomarkers detected. The device may include, without limitation, a substrate for mounting the nano-getter devices or any other suitable platform or method for maintaining the nano-getters in the tethered array, layer, or any other suitable arrangement. In such an architecture, the nano-getters bound with biomarkers may be diagnostic of a specific cancer or other physiological condition. This pattern-recognition approach, i.e., monitoring the pattern defined by multiple, simultaneously produced biomarker antigens, may be necessary in cases when detection of just one antigen cannot lead to a statistically significant diagnosis. See, for example, Z. Zhang et al., *Three biomarkers identified from serum proteomic analysis for the detection of early stage ovarian cancer*, Cancer Res., 64(16), pp. 5882-5890, which is incorporated herein by reference. Furthermore, such an architecture will allow simultaneous screening for multiple biomarkers, either for detection of several markers characteristic of a specific condition (e.g., cancer), or for multiple conditions.

In one exemplary embodiment, each of the dendrimers 40 is covalently tethered to the thin, strain-transducer film 30 by a covalent anchor group 70, which may be, for example, an alkane-thiol group or other suitable covalent anchor group. Other embodiments of the nano-getter device 10 may include one or more dendrimers 40 which encapsulate a semiconducting quantum dot and/or plasmonic metal-dielectric core-shell nanoparticle. In such embodiments, the semiconducting quantum dot or plasmonic particle would reside at the core of the dendrimer, providing another sensing modality, i.e. IR signature under strain (for QD) and/or surface plasmon resonance (SPR) signal upon protein adsorption to the ligand of the biomarker(s) specific to the cancer or other physiological condition.

In one exemplary embodiment of operation, the presence or absence of cancer (e.g., ovarian, cervical, prostrate, etc.) or other physiological condition, for example but not limited to, may be determined by analytical decomposition of reflected waveforms from external Raman excitation and/or the microwave induced ultrasound pulses, directed into the patient (e.g., peritoneal cavity). In embodiments using Raman excitation, the Raman signal directed into the patient is decomposed to identify detectable spectral shifts (a first cancer detection signature modality) that can be quantitatively related to a characteristic strain in the Raman-active SWNT-doped polymer strain-transducer film 30 imparted by dendrimer conformational changes upon selective binding to the one or more cancer-specific biomarkers.

In some exemplary embodiments, the Raman signal may be directed into the patient by coupling a Raman excitation source to a fiber-optic delivery and collection probe and laparoscopically inserting the probe with the Raman excitation source coupled therein into the patient (e.g., the peritoneal cavity) and directed at the tissue of interest. In other embodiments, where direct entry into the patient is not required, the probe with the Raman excitation (e.g., a diode laser) source coupled thereto may be inserted into an internal cavity of the patient (e.g., oral, rectal, and vaginal cavity) and directed at the tissue of interest. The Raman scattered light (from the patient) may be collected onto a holographic spectrograph coupled to a liquid nitrogen cooled, back-illuminated, deep depletion, charge-coupled device (CCD) camera. See, for example, Urs Utzinger et al., Near-Infrared Raman Spectroscopy For In Vivo Detection Of Cervical Precancers, *Applied Spectroscopy* v. 55, no. 8, 2001, pp. 955-959, which is incorporated herein by reference.

In exemplary embodiments using microwave induced ultrasound pulses, the microwave pulses directed into the body of the patient (e.g., the peritoneal cavity), serve as excitation/drive signals for the QCM RF oscillator 60 of the nanogetter device 10. The ultrasound pulses or waveform reflected back from the QCM RF oscillator 60 of the nano-getter device 10 (a detection signature modality) is decomposed to identify characteristic changes in the QCM resonant frequency, which is highly sensitive to changes in mass as the cancer-specific antigen (biomarker) binds to the antibody ligands of the dendrimers 40 of the nano-getter device 10.

In one exemplary embodiment, a threshold value for QCM signals, above a background or reference signal, which indicate the presence of cancer or pre-cancerous cells, is determined.

The nano-getter device 10 shown in FIG. 1, may also be used for detecting chemical and biological (biotoxins, etc.) analytes in various environments. Embodiments of nano-getter devices 10 used for chemical detection include dendrimer binding receptors 46 which are specifically selected for binding molecules of a chemical or biological analyte of interest to the dendrimers 40.

In some exemplary embodiments, the thin, strain-transducer film 30 of the nano-getter device 10 used for chemical detection, may comprise a thin film of piezoelectric material that generates a piezoelectric voltage. The piezoelectric material may include, without limitation, lead zirconate titanate, lead titanate, barium titanate, polyvinylidene fluoride, and gallium orthophosphate. In such embodiments, the piezoelectric strain-transducer film 30 may be independently powered by a battery or other suitable power source, provided locally as a component of the device 10. In other embodiments, the piezoelectric strain-transducer film 30 may be independently powered by a battery or other suitable power source located remotely from the device 10 and connected thereto by conventional cable means.

Although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention.

What is claimed is:

1. A nano-structured device for detecting a chemical or biological analyte, the device comprising:
   a carrier substrate;
   a transducer film disposed over a surface of the carrier substrate, the transducer film for generating a first signal in response to a mechanical stress applied thereto, the first signal indicating the detection of the chemical or biological analyte; and
   a dendrimer structure tethered to the transducer film, the dendrimer structure including a plurality of receptors for binding molecules of the chemical or biological analyte to the dendrimer structure,
   the dendrimer structure applying the mechanical stress to the transducer film, the mechanical stress being proportional to the strain induced into the dendrimer by the molecules of the chemical or biological analyte binding to the receptors, the transducer film generating the first signal indicating the detection of the chemical or biological analyte, the nano-structured device made of materials for in vivo use.

2. The nano-structured device of claim 1, wherein the first signal comprises a voltage.

3. The nano-structured device of claim 1, wherein the transducer film comprises a piezoelectric film and the first signal comprises a piezoelectric voltage.

4. The nano-structured device of claim 1, wherein the transducer film comprises a Raman-active film and the first signal comprises a spectral Raman shift responsive to an induced strain in the transducer film.

5. The nano-structured device of claim 1, wherein the first signal is proportional to the stress applied to the transducer film.

6. The nano-structured device of claim 1, wherein the strain induced into the dendrimer by the molecules of the chemical or biological analyte binding to the receptors is proportional to the quantity of the molecules of the chemical or biological analyte binding to the receptors.

7. The nano-structured device of claim 1, wherein the carrier substrate generates a second signal which changes in proportion to a mass increase of the nano-structured device, the mass increase proportional to the quantity of molecules binding to the dendrimer structure via the receptors, the second signal indicating the detection of the chemical or biological analyte.

8. The nano-structured device of claim 1, wherein the second signal comprises a resonant harmonic frequency signal.

9. The nano-structured device of claim 1, wherein the carrier substrate comprises a quartz crystal and the second signal comprises a resonant harmonic frequency signal.

10. The nano-structured device of claim 1, wherein the dendrimer structure comprises an array of at least one or more types of dendrimers.

11. The nano-structured device of claim 1, wherein the dendrimer structure comprises a film formed by a tethered layer of dendrimers.

12. The nano-structured device of claim 1, wherein the receptors are formed by end-functionalization of the dendrimer structure.

13. A nano-structured device for detecting a chemical or biological analyte, the device comprising:
    a carrier substrate for generating a signal which changes in proportion to a mass increase of the nano-structured device, the signal indicating the detection of the chemical or biological analyte;
    a transducer film disposed over a surface of the carrier substrate; and
    a dendrimer structure tethered to the transducer film, the dendrimer structure including a plurality of receptors for binding molecules of the chemical or biological analyte to the dendrimer structure,
    the mass increase proportional to the quantity of molecules binding to the dendrimer structure via the receptors, the signal indicating the detection of the chemical or biological analyte, the nano-structured device made of materials for in vivo use.

14. The nano-structured device of claim 13, wherein the signal comprises a resonant harmonic frequency signal.

15. The nano-structured device of claim 13, wherein the carrier substrate comprises a quartz crystal and the signal comprises a resonant harmonic frequency signal.

16. The nano-structured device of claim 13, wherein the at least one dendrimer structure comprises a tethered layer of at least one or more types of dendrimers.

17. The nano-structured device of claim 13, wherein the dendrimer structure comprises a film formed by a tethered layer of dendrimers.

18. The nano-structured device of claim 13, wherein the receptors are formed by end-functionalization of the dendrimer structure.

19. The nano-structured device of claim 1 formed of materials capable of being implanted within a human.

20. The nano-structured device of claim 1 formed of materials capable of being implanted within an animal.

21. The nano-structured device of claim 1 wherein the signal produced is capable of being transferred outside a body.

22. The nano-structured device of claim 1 wherein the transducer film produces a second signal indicating the detection of the chemical or biological analyte.

23. The nano-structured device of claim 13 formed of materials capable of being implanted within a human.

24. The nano-structured device of claim 13 formed of materials capable of being implanted within an animal.

25. The nano-structured device of claim 13 wherein the signal produced is capable of being transferred outside a body.

26. The nano-structured device of claim 13 wherein the transducer film produces a second signal indicating the detection of the chemical or biological analyte.

* * * * *